United States Patent [19]

di Pietro et al.

[11] Patent Number: 4,481,012

[45] Date of Patent: Nov. 6, 1984

[54] PROCESS FOR THE PRODUCTION OF A MIXTURE OF METHANOL AND HIGHER ALCOHOLS OF "FUEL GRADE"

[75] Inventors: Raffaele di Pietro, Milan; Alberto Paggini, Spino d'Adda; Vincenzo Lagana', Milan, all of Italy

[73] Assignee: Snamprogetti S.p.A., Milan, Italy

[21] Appl. No.: 514,544

[22] Filed: Jul. 18, 1983

Related U.S. Application Data

[63] Continuation of Ser. No. 269,708, Jun. 2, 1981, abandoned, which is a continuation-in-part of Ser. No. 215,172, Dec. 11, 1980, abandoned.

[30] Foreign Application Priority Data

May 16, 1980 [IT] Italy ................................ 22116 A/80

[51] Int. Cl.³ .................................................. C10L 1/18
[52] U.S. Cl. .......................................... 44/53; 44/54; 518/705; 518/713; 518/714; 518/728
[58] Field of Search .................. 44/53, 54; 518/705, 518/714, 728, 713; 203/43

[56] References Cited

U.S. PATENT DOCUMENTS

| | | | |
|---|---|---|---|
| 1,569,775 | 1/1926 | Mittasch | 518/713 |
| 1,791,568 | 2/1931 | Mittasch | 518/713 |
| 2,010,005 | 8/1935 | Berliner | 44/54 |
| 3,763,205 | 10/1973 | Green | 518/713 |
| 3,940,428 | 2/1976 | Connell et al. | 518/705 |
| 3,950,369 | 4/1976 | Gent | 518/713 |

*Primary Examiner*—Jacqueline V. Howard
*Attorney, Agent, or Firm*—Morgan, Finnegan, Pine, Foley & Lee

[57] ABSTRACT

A process for the production of a mixture of methanol and higher alcohols of "fuel grade" from CO and $H_2$.

To reduce the water content in the mixture coming from the synthesis reactor of the synthesis of the alcohols, the reaction product is cooled down and is fed to a secondary reactor wherein the conversion reaction $$CO + H_2O \rightleftharpoons CO_2 + H_2$$

is carried on in conditions near to equilibrium.

The further product of reaction is cooled in a more thorough manner so as to obtain a liquid phase constituted by the "fuel grade" mixture of alcohols and a gaseous phase which after the discharge of the inert substances and after elimination of the $CO_2$ is recycled to the synthesis reactor.

In the secondary conversion reactor operation is carried out with a temperature comprised between 150° C. and 250° C., at a pressure equal to that of the synthesis reactor and in the presence of a copper catalyst.

14 Claims, 1 Drawing Figure

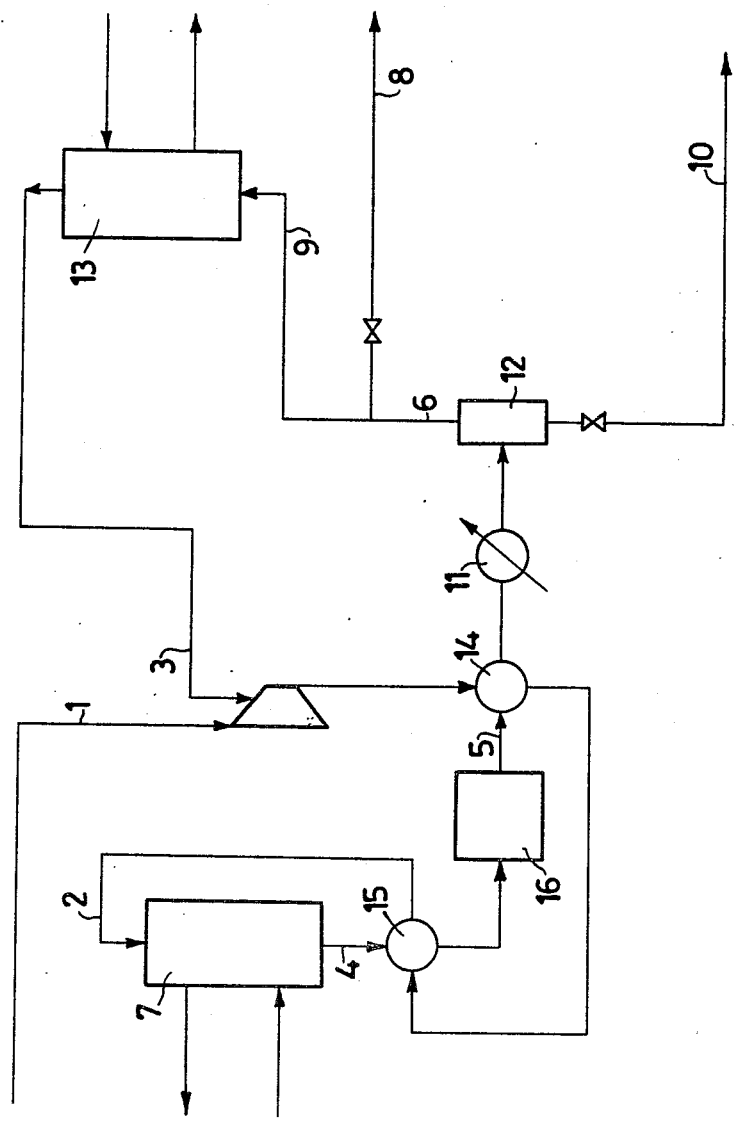

PROCESS FOR THE PRODUCTION OF A MIXTURE OF METHANOL AND HIGHER ALCOHOLS OF "FUEL GRADE"

This is a continuation of application Ser. No. 269,708, filed June 2, 1981, which is, in turn, a continuation-in-part application of Ser. No. 215,172 filed Dec. 11, 1980, now abandoned.

The instant invention relates to a process for the production of a "fuel grade" mixture of methanol and higher alcohols.

It is known that methanol may be employed alone, or in admixture with gasoline, as a fuel.

It has been found that the use of methanol in admixture with gasoline is made prohibitive by the amount of water that is present in both the refining plants and in the circuit of distribution of the fuel: at low temperature and in the presence of very small amounts of water the methanol tends to demix forming an aqueous phase rich with methanol and a hydrocarbon phase thereby rendering its use non-advisable.

It is known that this inconvenience can be overcome by the use of suitable solubilizers, in particular the $C_2$, $C_3$, $C_4$, $C_5$, $C_6$ alcohols have been indicated.

These alcohols can be produced separately (they are available in the trade but at high prices) and added to the methanol or they may be co-produced together with methanol and this latter solution is the one held to be more economic. It is known in fact that if modifying conveniently the catalysts of methanol production both those of the high temperature process, Zn, Cr type, and those of the lower temperature process, based on Cu, it is possible to obtain from hydrogen and carbon oxides, contemporaneously a mixture of methanol, higher alcohols and water.

Water is produced both in the reaction forming the higher alcohols $$2CO + 4H_2 \rightleftharpoons C_2H_5OH + H_2O \tag{1}$$

$$3CO + 6H_2 \rightleftharpoons C_3H_7OH + 2H_2O \tag{2}$$

$$4CO + 8H_2 \rightleftharpoons C_4H_9OH + 3H_2O \tag{3}$$

and in the reaction forming methanol from $CO_2$, that may possibly be present in the feed:

$$CO_2 + 3H_2 \rightleftharpoons CH_3OH + H_2O \tag{4}$$

Since, as we have seen, the function of the higher alcohols is to keep the methanol in solution in the gasoline in the presence of water, it is important, in order not to add fresh water to the system, that the mixture of methanol and higher alcohols should contain the lowest possible amount of water.

By "fuel grade" mixture of methanol and higher alcohols there is intended just a mixture meeting these requirements namely that the amount of water should be of the order of a thousand ppm.

The $C_2$, $C_3$, $C_4$, $C_5$ higher alcohols form azeotropes with water and, therefore, the lowering of the water content from the level of some %, as present in the mixture after cooling and condensing of the gas, down to a level of a thousand ppm as required by the fuel grade, is a difficult and costly operation.

Present-day technique teaches to separate the water from this mixture by means of an azeotropic distillation with the use of cyclohexane, benzene, or other azeotropic agents.

Now it has surprisingly been found that it is possible to obtain a mixture of methanol and higher alcohols of fuel grade, from carbon monoxide and hydrogen, already after the cooling and the condensing of the reacted gas, thereby avoiding having to resort to the step of azeotropic distillation, which is very burdensome both as cost and as energy consumption.

The accompanying FIGURE is a flow diagram showing schematically methanol synthesis process according to the invention.

It is an object of the present invention to provide a process for producing fuel grade mixtures of methanol and higher alcohols and comprising:

(a) feeding to a synthesis reactor a gaseous mixture essentially constituted by CO and $H_2$;
(b) cooling the reaction mixture constituted by methanol higher alcohols and water as well as by unreacted gases;
(c) sending the latter mixture to a conversion reactor;
(d) cooling the further reaction product constituted by methanol, higher alcohols, unreacted gases, carbon dioxide and traces of water;
(e) separating a liquid phase constituted by the "fuel grade" alcoholic mixture and a gaseous phase essentially constituted by CO, $H_2$ and $CO_2$;
(f) recycling the gaseous phase to the synthesis reactor after the elimination of the $CO_2$.

More particularly it is an object of the present invention to provide a process for producing a fuel grade alcoholic mixture according to which the mixture of reacted gas leaving the synthesis reactor, is fed after previous cooling to a second reactor where on a conversion catalyst of conventional kind the reaction:

$$CO + H_2O \rightleftharpoons CO_2 + H_2 \tag{5}$$

is carried on in conditions near to equilibrium.

This solution, which may be effected even with one reactor only, enables to reduce the amount of water, produced according to the reactions (1), (2), (3) and (4), to such values that when the reacted gas is cooled and the condensed product is separated from the gaseous phase, in the liquid there remains only an amount of $H_2O$ at a level of one thousand ppm (fuel grade mixture).

Since the conversion per passage is low, it is necessary to recycle the unreacted gas to the synthesis reactor, as well as to discharge a part of the gas in order to avoid accumulation of inert matter.

Owing to the recycle the $CO_2$ produced according to reaction (5), there would be feed back to the reactor, whence it is necessary to resort to its removal in order to get the same situation at every passage.

Hence the gas leaving the conversion reactor is cooled and then after having separated the condensed product is sent to a separating column where the $CO_2$ is absorbed by a suitable system.

Now the recycle gas is put together with the fresh gas and then fed again to the synthesis reactor. In order to keep the inert content constant in the synthesis loop before and after the absorption of $CO_2$, a certain amount of gas will have to be discharged. The $CO_2$ wash may be carried out with any known system for instance with suitable solvents with the possible necessity of introducing a frigorific cycle on the recycle gas in order to abate the methanol vapours when the latter interfere with the absorption system.

According to the process of the present invention the synthesis gas, containing mainly CO and $H_2$ and traces of $CO_2$, $N_2$ and $CH_4$, is sent to the synthesis reactor for the production of methanol and higher alcohols.

The synthesis reactor is able to operate both at high pressure and at low pressure, whence in the former case the synthesis of the alcoholic mixture takes place at a temperature which is generally comprised between 300° C. and 500° C., preferably between 360° C. and 420° C., and at a pressure higher than 150 ata, preferably higher than 200 ata; in the latter case the synthesis takes place at a temperature comprised between 200° C. and 300° C., preferably between 230° C. and 270° C., and at a pressure comprised between 30 and 150 ata, preferably between 50 and 100 ata.

The catalysts are those used and adapted for the production of methanol and more particularly of the type of zinc, chromium in the former case, and of the type of copper, zinc, with Al and/or Cr and/or V and/or Mn in the latter case, properly modified with alkali metals and/or alkaline earth metals to encourage the synthesis of the higher alcohols.

From the synthesis reactor the gaseous mixture is sent, after previous cooling with heat recovery, to a conversion reactor where, in the presence of a copper catalyst the reaction (5) is carried on in conditions near to its equilibrium.

In the conversion reactor the pressure is equal to the pressure in the synthesis reactor whilst the temperature is sensibly lower and is comprised between 150° C. and 250° C., preferably between 160° C. and 220° C.

At the reactor outlet (of the conversion reactor) the gaseous mixture is cooled in such a manner as to separate a liquid phase constituted by the fuel grade mixture of methanol and higher alcohols and a gaseous phase which after discharging the inert matter and absorbing the $CO_2$ produced according to reaction (5) in the conversion reactor, is recycled to synthesis together with the fresh feed.

In FIG. (1) there is shown a flow sheet in accordance with the instant invention:

The synthesis gas (1) and the recycle gas (3) are brought to the operating pressure and are fed through (2) to the reactor (7); the reaction product leaves the synthesis reactor by means of the line (4) and after a cooling in (15) it is sent to the conversion reactor (16) where its water content is sensibly reduced.

The reacted gas leaves the conversion reactor by means of the line (5), is sent first to the heat recuperator (14) than to the condenser (11) and then to the separator (12) from the basis of which there is extracted, through (10), the fuel grade alcoholic mixture, and from the head, through (6), a gaseous phase which in part is discharged (8) and in part (9) is sent to the section of absorption of the $CO_2$ (13) and then recycled to the synthesis reactor.

Now some Examples are given which have the purpose of illustrating the invention, without limiting its scope.

It should be observed that the liquid mixture of methanol and higher alcohols as obtained with the process according to this invention has a limpidity which is comparable to that of the commercial gasolines, absence of dyestuffs and of unpleasant smells which are experienced, for example, in the alcohol mixtures as obtained with the Fischer-Tropsch synthesis.

EXAMPLE 1

Operation is effected according to the flow sheet of FIG. 1; to the synthesis reactor, there is fed, together with the recycle gas, a gaseous mixture constituted by:

|  | $Nm^3/h$ | % by volume |
| --- | --- | --- |
| CO | 6055.9 | 41.40 |
| $CO_2$ | 0.27 | traces |
| $H_2$ | 8509.2 | 58.10 |
| $N_2$ | 55.72 | 0.38 |
| $CH_4$ | 18.3 | 0.12 |

Synthesis Reaction

The catalyst has the following composition:
ZnO 72.1% by wt.; $Cr_2O_3$, 25.9% and $K_2O$: 2.0%.
Catalyst: 10 cubic meters are used, Temp. 410° C.—pressure 260 atm. The composition at point (2) of the flowsheet FIG. 1 is as follows:

| | |
| --- | --- |
| CO = 46.985% by vol: | 33190.4 Nor. Cu. Meters an Hour |
| $CO_2$ = 0.04% | 30 |
| $H_2$ = 46.985% | 33190.4 |
| $N_2$ = 5.14% | 3636.1 |
| $CH_4$ = 0.85% | 601.1 |
| $CH_3OH$ Traces | Traces Total 70648.82 Nor. Cu. Meters an Hour |
| GHSV = 7064.9/Hour | |

Conversion Reaction

Twenty Cu. Meters of catalyst are used, which has the following composition, by weight:
ZnO=31.4%, $Cr_2O_3$=49.9%, Cu Oxide=18.7%
GHSV: 3073.4/Hour, pressure 260 atm., temp. 200° C.

After the synthesis reaction in reactor (7), the heat recovery in (15) and the conversion reaction in reactor (16), there is obtained a product constituted by:

|  | $Nm^3/h$ | % by volume |
| --- | --- | --- |
| CO | 27599.2 | 44.84 |
| $CO_2$ | 1031.7 | 1.68 |
| $H_2$ | 25013.1 | 40.80 |
| $N_2$ | 3636.1 | 5.92 |
| $CH_4$ | 601.1 | 0.97 |
| $CH_3OH$ | 3159.8 | 5.10 |
| $C_2H_5OH$ | 67.2 | 0.11 |
| $C_3H_7OH$ | 119.5 | 0.19 |
| $C_4H_9OH$ | 234.4 | 0.38 |
| $H_2O$ | 7.7 | 0.01 |

This reaction product is sent, after previous cooling, to the separator (12) from the basis of which there is recovered, with (10), the fuel grade alcoholic mixture having the following composition:

|  | kg/h | % by weight |
| --- | --- | --- |
| $CH_3OH$ | 4508 | 78.5 |
| $C_2H_5OH$ | 138 | 2.4 |
| $C_3H_7OH$ | 320 | 5.57 |
| $C_4H_9OH$ | 773 | 13.4 |
| $H_2O$ | 6 | 0.1 |

EXAMPLE 2 (COMPARATIVE)

This Example shows how it is important to select the operation conditions of the conversion reactor; if the temperature of this reactor were equal to that of the synthesis reactor one would obtain an alcoholic mixture with 7.600 ppm of $H_2O$, too high a value to consider the mixtire to be of fuel grade.

For the sake of simplicity we suppose to eliminate in the flow sheet of FIG. 1, the heat recuperator (15) and to effect the synthesis reaction and the conversion reaction in the single reactor (7).

To the synthesis reactor, together with the recycle gas, there is fed a gaseous mixture constituted by:

|  | $Nm^3/h$ | % by volume |
|---|---|---|
| CO | 6008.2 | 41.14 |
| $CO_2$ | 0.27 | traces |
| $H_2$ | 8556.9 | 58.45 |
| $N_2$ | 55.72 | 0.38 |
| $CH_4$ | 18.3 | 0.12 |

The synthesis catalyst is as in Example 1 hereof with the same temperatures, pressures and space velocity hourly (GHSV) whereas the conversion catalyst is a commercial catalyst Sk-12 made by Topsøe (iron oxide promoted with chromium oxide).

Temperature 410° C., pressure 260 atm., 20 cu. meters of catalyst, GHSV=3.073.4/hour.

From the reactor there is recovered a reaction product having the following composition

|  | $Nm^3/h$ | % by volume |
|---|---|---|
| CO | 27646.9 | 44.98 |
| $CO_2$ | 984 | 1.61 |
| $H_2$ | 24965.4 | 40.62 |
| $N_2$ | 3636.1 | 5.92 |
| $CH_4$ | 601.1 | 0.97 |
| $CH_3OH$ | 3159.82 | 5.14 |
| $C_2H_5OH$ | 67.24 | 0.1 |
| $C_3H_7OH$ | 119.5 | 0.19 |
| $C_4H_9OH$ | 234.38 | 0.38 |
| $H_2O$ | 55.38 | 0.09 | which after cooling gives an alcoholic mixture having the following composition:

|  | kg/h | % by weight |
|---|---|---|
| $CH_3OH$ | 4508 | 77.98 |
| $C_2H_5OH$ | 138 | 2.38 |
| $C_3H_7OH$ | 320 | 5.51 |
| $C_4H_9OH$ | 773.8 | 13.37 |
| $H_2O$ | 44.5 | 0.76 |

EXAMPLE 3

This Example shows that even if one wants to produce an alcoholic mixture with a higher content of higher alcohols it is still possible to obtain a fuel grade mixture according to the scheme of our patent.

Since a higher production of higher alcohols means also to have more $H_2O$ by this Example it is proved that the amount of $H_2O$ in the product does not depend considerably on the amounts present in the reacting gas in the post-reactor, but on the reaction conditions of the latter.

Since a mixture with higher content of higher alcohols can be obtained not only with a different catalyst for synthesis but also by selecting different operating conditions, it follows that what is illustrated in our patent remains valid anyway whatsoever the composition of the synthesized mixture may be, or, in other words, that the solution proposed by our application is indipendent of the synthesis catalyst adopted, as well as of the operative conditions of synthesis.

The synthesis reactor is fed by the recycle gas together with a gaseous mixture constituted by:

|  | $Nm^3/h$ | % by volume |
|---|---|---|
| CO | 6341.2 | 43.32 |
| $CO_2$ | 0.27 | traces |
| $H_2$ | 8223.9 | 56.17 |
| $N_2$ | 55.72 | 0.38 |
| $CH_4$ | 18.3 | 0.12 |

For the synthesis reaction, 12 cu meters of catalyst are used, the catalyst composition being as follows: ZnO=70.6% by wt., $Cr_2O_3$+25.4% by wt., $K_2O$=4.0%, pressure 200 atm., temp. 400° C., GHSV: 5887.4/hour. For the conversion reaction, 20 cu. meters of catalyst are used, the catalyst composition, in % by weight being as follows: ZnO-53.7%, Cu Oxide=32.8%, $Al_2O_3$, 13.5%, temp. 180° C., press. 200 atm., GHSV: 3073.4/hour.

After the synthesis reaction in reactor (7), the heat recovery in (15) and the conversion reaction in the reactor (16), a product is obtained which is formed by:

|  | $Nm^3/h$ | % by volume |
|---|---|---|
| CO | 27313.9 | 44.45 |
| $CO_2$ | 1317 | 2.16 |
| $H_2$ | 25298.4 | 41.15 |
| $N_2$ | 3636.1 | 5.92 |
| $CH_4$ | 601.1 | 0.97 |
| $CH_3OH$ | 2702.8 | 4.39 |
| $C_2H_5OH$ | 134.3 | 0.21 |
| $C_3H_7OH$ | 205.8 | 0.33 |
| $C_4H_9OH$ | 250.4 | 0.40 |
| $H_2O$ | 10 | 0.02 |

This product condensed provides an alcoholic mixture having the following composition:

|  | kg/h | % by weight |
|---|---|---|
| $CH_3OH$ | 3855.5 | 69.88 |
| $C_2H_5OH$ | 275.5 | 4.99 |
| $C_3H_7OH$ | 551 | 9.99 |
| $C_4H_9OH$ | 826.6 | 14.98 |
| $H_2O$ | 8.03 | 0.16 |

We claim:

1. In a continuous process for the production of a fuel grade mixture consisting essentially of methanol, higher alcohols and traces of water, which process comprises feeding a gaseous mixture consisting essentially of carbon monoxide and hydrogen to a synthesis reactor, said reactor operating at a temperature of about 200° C. to about 500° C. and a pressure higher than 30 atm; reacting said gaseous mixture in said synthesis reactor to form a reaction mixture which consists essentially of methanol, higher alcohols, water and unreacted gases; and cooling said reaction mixture, the improvement which comprises:

(a) feeding said cooled reaction mixture to a conversion reactor which operates at substantially the same pressure as said synthesis reactor and a temperature of from about 150° C. to about 250° C.;
(b) reacting in said conversion reactor the carbon monoxide and water in said cooled reaction mixture to form carbon dioxide and hydrogen according to the conversion reaction $$CO + H_2O \rightleftharpoons CO_2 + H_2$$

to form a reaction product consisting essentially of methanol, higher alcohols, unreacted starting gases; carbon dioxide and traces of water;
(c) cooling said reaction product to form a liquid phase comprising said fuel grade mixture and a gaseous phase consisting essentially of carbon monoxide, hydrogen and carbon dioxide;
(d) separating said liquid phase and said gaseous phase;
(e) removing carbon dioxide from said gaseous phase;
(f) recycling the gaseous phase product from step (e) to said synthesis reactor as said gaseous feed mixture.

2. A process according to claim 1 wherein the synthesis reactor operates at a temperature between 330° C. and 500° C.

3. A process according to claim 1 wherein the synthesis reactor operates at a pressure higher than 150 atm.

4. A process according to claim 2 wherein the temperature is between 360° C. and 420° C.

5. A process according to claim 3 wherein the pressure is higher than 200 atm.

6. A process according to claim 1 wherein the synthesis reactor operates at a temperature between 200° C. and 300° C.

7. A process according to claim 1 wherein the synthesis reactor operates at a pressure between 30 and 150 atm.

8. A process accoding to claim 6 wherein the temperature is between 230° C. and 270° C.

9. A process according to claim 8 wherein the pressure is selected preferably between 50 and 100 atm.

10. A process according to claim 1 wherein the conversion reactor operates at a temperature between 150° C. and 250° C.

11. A process according to claim 10 wherein the temperature is between 160° C. and 220° C.

12. A process according to claims 2 or 3 wherein the synthesis reaction takes place in the presence of a catalyst based on zinc and chromium modified with alkali metals and/or with alkaline earth metals.

13. A process according to claims 6 or 7 wherein the synthesis reaction takes place in the presence of a catalyst based on copper, zinc and with Al and/or Cr and/or V and/or Mn modified with alkali metals and/or alkaline earth metals.

14. A process according to claim 10 wherein the conversion reaction takes place in the process of a copper conversion catalyst.

* * * * *